(12) United States Patent
Alami et al.

(10) Patent No.: US 6,392,080 B1
(45) Date of Patent: *May 21, 2002

(54) PROCESS FOR THE PREPARATION OF A CYANOBIPHENYL

(75) Inventors: Mouad Alami, Bussy St Georges; Gérard Cahiez, Paris; Bertrand Castro, Saint Aunes; Eric Riguet, Les Ulis, all of (FR)

(73) Assignee: Sanofi-Stnthélabo, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/147,787

(22) PCT Filed: Sep. 8, 1997

(86) PCT No.: PCT/FR97/01577

§ 371 Date: Jun. 30, 1999

§ 102(e) Date: Jun. 30, 1999

(87) PCT Pub. No.: WO98/09941

PCT Pub. Date: Mar. 12, 1998

(30) Foreign Application Priority Data

Sep. 9, 1996 (FR) .............................. 96 10970

(51) Int. Cl.$^7$ ............................................ C07C 255/50
(52) U.S. Cl. ...................................................... 558/378
(58) Field of Search .......................................... 558/378

(56) References Cited

U.S. PATENT DOCUMENTS 5,288,895 A * 2/1994 Bousset et al. ............. 558/378

FOREIGN PATENT DOCUMENTS

| EP | 0 341 514 | 11/1989 |
|----|-----------|---------|
| EP | 0 470 794 | 2/1992  |
| EP | 0 566 468 | 10/1993 |
| EP | 0 571 770 | 12/1993 |
| EP | 0 253 310 | 10/1994 |

* cited by examiner

*Primary Examiner*—Floyd D. Higel
*Assistant Examiner*—Ebenezer Sackey
(74) *Attorney, Agent, or Firm*—Jacobson Holman, PLLC

(57) ABSTRACT

The subject-matter of the invention is a process for the preparation of o-(p-tolyl)benzonitrile, characterized in that an o-halobenzonitrile is treated with a p-tolylmagnesium halide in the presence of a manganous salt and of a cocatalyst comprising a transition metal.

17 Claims, No Drawings

PROCESS FOR THE PREPARATION OF A CYANOBIPHENYL

This application is a 371 of PCT/FR97/01577 filed Sep. 8, 1997.

The present invention relates to a process for the preparation of a cyanobiphenyl.

More particularly, the subject-matter of the invention is a process for the preparation of o-(p-tolyl)benzonitrile of formula I

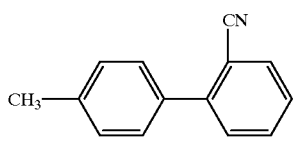

which constitutes the key intermediate in the synthesis of numerous active principles of medicines acting in particular against hypertension by a mechanism in which angiotensin II is inhibited.

o-(p-Tolyl)benzonitrile, hereinafter denoted more concisely as orthotolylbenzonitrile or OTBN, was disclosed for the first time in EP 253,310 and a number of processes for its synthesis have recently been provided.

The process which seems to be the most appropriate for the preparation of OTBN is disclosed in EP 566,468 and consists of the reaction of an o-halobenzonitrile with a p-tolylmagnesium halide in the presence of a manganous salt, preferably $MnCl_2$. This method, with respect to those known previously, has the advantage of taking place in a single stage with yields of approximately 70% before crystallization. However, it gives 4,4'-dimethylbipohenyl, resulting from the condensation of the p-tolylmagnesium halide with itself, as reaction by-product.

It has now been found that, if the reaction between the p-tolylmagnesium halide and the o-halobenzonitrile is carried out in the presence of a manganous salt and of traces of a palladium(II) salt, the OTBN is obtained with a yield of at least approximately 92% while the 4,4'-dimethylbiphenyl impurity falls below approximately 2.5%.

Thus, the subject-matter of the present invention is a process for the preparation of o-(p-tolyl)benzonitrile, characterized in that an o-halobenzonitrile, preferably o-bromobenzonitrile, is treated with a p-tolylmagnesium halide in the presence of a manganous salt and of a cocatalyst comprising a transition metal, preferably a palladium(II) salt.

The coupling reaction according to the invention is carried out in a solvent of the ether type, such as methyl t-butyl ether, dibutyl ether, dioxane or tetrahydrofuran, it being possible for the reaction temperature to vary from −10 to 60° C., depending on the solvent employed.

This reaction results in the transient formation of a complex, which is hydrolysed according to known procedures, for example by means of an acid, such as hydrochloric acid.

As regards the manganous salt, it is preferably $MnCl_2$ or $MnCl_4Li_2$, it being possible for the latter to be formed in situ by addition of two molar equivalents of LiCl and of one molar equivalent of $MnCl_2$.

This manganous salt takes part in the reaction in a proportion of 0.5 to 1.3 molar equivalents per molar equivalent of starting o-halobenzonitrile.

The transition metal forming the cocatalyst is advantageously nickel, cobalt, platinum or, in particular, palladium.

Use is preferably made, as cocatalyst comprising a transition metal, of a palladium(II) salt, in particular the nitrate, chloride, acetate, bromide, sulphate or the like, the chloride ($PdCl_2$) and the acetate ($CH_3$—COO—Pd—OOC—$CH_3$) being particularly advantageous. The palladium salt is preferably complexed, for example with at least one organophosphorus compound comprising trivalent phosphorus. Mention may more particularly be made of palladium complexes, such as bis(triphenylphosphine)-dichloro-, bis(tributylphosphine)dichloro-, bis(tri-cyclohexylphosphine) dichloro-, diallyltriphenyl-phosphinedichloro-, triphenylphosphinepiperidine-dichloro-, bis(cyclohexyloxime)dicarbonyl-, 1,5,9-cyclododecatrienedichloro-, bis(triphenylphosphine)-dicarbonyl-, bis(triphenylphosphine) diacetate-, bis(triphenylphosphine) sulphate- or (2,4-pentanedione) -tetrakis(triphenylphosphine)palladium. Among these, palladium(II) complexes are particularly advantageous, 1,3-bis(diphenylphosphino)propane (dppp) complexed with palladium(II) chloride or palladium(II) acetate being preferred.

The palladium salts and the organophosphorus compounds can be added separately to the reaction mixture.

In this case, the amount of organophosphorus compound is preferably sufficient to form the cocatalyst in situ in the form of a complex with the palladium present. The said complex is generally prepared so that the P/Pd ratio is approximately 1/1, but such a ratio can vary between 0.5/1 and 2/1 without having a significant detrimental effect on the result of the process.

This cocatalyst is present in very small amounts in the reaction mixture, namely from 0.001 to 2 molar % per mole of starting o-halobenzonitrile.

According to a preferred procedure, the p-tolylmagnesium halide is in equimolar amounts or in slight excess (1 to 1.5 mol) with respect to the o-halobenzonitrile. In addition, the preferred manganous catalyst ($MnCl_4Li_2$) is formed either in situ, in equimolar amounts or in slight excess (1 to 1.5 mol) with respect to the o-halobenzonitrile, or at the time of use, before addition to the reaction mixture.

$MnC:L_4Li_2$ is prepared by reacting one equivalent of $MnCl_2$ with two equivalents of LiCl.

The reaction can be carried out in tetrahydrofuran by adding, at a temperature of 10° C., the cocatalyst and the o-halobenzonitrile, optionally in solution in tetrahydrofuran, to a tetrahydrofuran solution comprising the p-tolylmagnesium halide and the manganous catalyst. This reaction, which is exothermic, can be controlled by adjusting the rate of addition of the substituted benzonitrile and of the cocatalyst, so as to maintain it below 35° C.

Alternatively, the reaction can also be carried out by adding the p-tolylmagnesium halide in, for example, tetrahydrofuran to a mixture of o-halobenzonitrile, cocatalyst and manganous catalyst in, for example, tetrahydrofuran. In this case, the reaction temperature can be better controlled and the addition of p-tolylmagnesium halide can be carried out even at a higher temperature, about 50–55° C., so as to decrease the duration of the reaction and the amount of cocatalyst employed.

However, in order to improve the progress of the reaction, it can be advantageous to add a cosolvent to the mixture comprising the manganous catalyst. This cosolvent is preferably another ether or diether, for example dimethoxyethane.

According to the above preferred procedure, hydrolysis is carried out in situ with hydrochloric acid and the OTBN thus formed is isolated according to conventional techniques, for example by extraction with a suitable solvent, evaporation of the solvent and purification by crystallization from ethanol or by chromatography.

The OTBN is thus obtained with very high yields, from 92 to 98% depending on the proportions of the reactants employed. It comprises very small amounts of 4,4'-dimethylbiphenyl, generally less than 2.5%.

The amount of 4,4'-dimethylbiphenyl which is formed according to the process of the present invention was compared with that which is formed according to the process disclosed in EP 566,468. Thus, by carrying out the reaction:

according to EP 566,468, namely by using $MnCl_2$ alone as catalyst, in a series of tests under the same conditions, the 4,4'-dimethylbiphenyl by-product was obtained with a yield of 8 to 12% with respect to the p-tolylmagnesium bromide, i.e. 6.5 to 10% by weight of 2-(p-tolyl)benzonitrile final product; according to the present invention, namely by using $MnCl_2$ end $PdCl_2$/dppp as catalyst and cocatalyst, in a series of tests under the same conditions, the 4,4'-dimethylbiphenyl by-product was obtained with a yield of 0.5 to 1% with respect to the p-tolylmagnesium bromide, i.e. at most 0.65% by weight of final product.

The cocatalyst comprising a transition metal can also be a cobalt, nickel or platinum salt, as indicated above. In the case of a cocatalyst comprising nickel, use is generally made of a nickel(II) salt, such as nickel chloride or acetylacetonate. This salt is preferably complexed with at least one organophosphorus compound comprising trivalent phosphorus, such as a phosphine, for example triphenylphosphine. The nickel salt and the organophosphorus compound can be added separately to the reaction mixture. This nickel-comprising cocatalyst is advantageously pretreated with a reducing agent, such as a hydride, for example dibutylaluminium hydride or diisobutylaluminium hydride, or alternatively with a methylmagnesium halide, for example methylmagnesium chloride, so as to form catalysts comprising Ni(O), such as $Ni[P(C_6H_5)_3]_4$. Systems comprising nickel acetylacetonate, triphenylphosphine and diisobutylaluminium hydride have proved to be particularly advantageous.

The following non-limiting examples illustrate the invention. In these examples, the molar percentages of cocatalyst are calculated with respect to the amount of ortho-halobenzonitrile.

EXAMPLE 1

$MnCl_2$ (0.65 g, 5.14 mmol) and LiCl (0.44 g, 10.28 mmol) are added successively, under a nitrogen atmosphere and at room temperature, to 2 ml of anhydrous tetrahydrofuran. The mixture is stirred until the salts have dissolved (formation of $MnCl_4Li_2$). A solution of p-tolylmagnesium chloride in tetrahydrofuran (1.80N, 2.86 ml, 5.14 mmol) is then added so that the temperature is maintained between −100° C. and 0° C. Dimethoxyethane (1 ml, 10.28 mmol) is then rapidly added at 0° C. and the organomanganous compound thus obtained is kept stirring for 5 min at +100° C.

1/1: $PdCl_2$/dppp (0.023 g, 1 mol %) is added and then o-bromobenzonitrile (0.72 g, 3.955 mmol) is added. The temperature rises from +10 to +300° C. over 15 min and then slowly falls to +250° C. After stirring for 3 hours at room temperature, the reaction mixture is hydrolysed using a 1N hydrochloric acid solution (15 ml). After extracting with ethyl ether, the organic phase is dried over potassium carbonate, filtered and then evaporated under vacuum. The oil thus formed is subsequently purified by chromatography (silica: 20 g; eluant: petroleum ether/ethyl acetate=95/5). The o-(p-tolyl)benzonitrile thus obtained is then harvested, with a yield of 96%, in the form of off-white crystals.

Melting point: +48° C.; $^1$H NMR ($CDCl_3$) δ2.42 (s, 3H, $CH_3$); $^{13}$C NMR ($CDCl_3$) δ21.03, 110.85, 118.70, 127.09, 128.39, 129.22, 129.74, 132.60, 133.47, 135.03, 138.43, 145.20.

EXAMPLES 2 and 3

By carrying out the preparation as described in Example 1, while using 0.5 equivalents of $MnCl_4Li_2$ and 1.3 equivalents of p-tolylmagnesium chloride per one equivalent of o-halobenzonitrile and while varying the amount of 1/1: $PdCl_2$/dppp, the o-(p-tolyl)benzonitrile yields shown in Table 1 were obtained.

TABLE 1

| Example | 1/1 $PdCl_2$/dppp (molar %) | Stirring time at room temperature | Yield of isolated product |
|---------|------------------------------|-----------------------------------|---------------------------|
| 2 | 1 | 90 minutes | 95% |
| 3 | 0.5 | 5 hours | 92% |

EXAMPLE 4

A suspension of $MnCl_2$ (0.25 g, 1.98 mmol) and LiCl (0.17 g, 3.955 mmol) in a mixture of 2 ml of anhydrous tetrahydrofuran and 0.38 ml of dimethoxyethane (3.955 mmol) is stirred at room temperature. After stirring for approximately 30 minutes, a homogeneous medium is obtained. The addition is then so carried out of 1/1: $PdCl_2$/dppp (0.023 g, 1 mol %) and of o-bromobenzonitrile (0.72 g, 3.955 mmol) and then a solution of p-tolylmagnesium chloride in tetrahydrofuran (1.80N, 2.86 ml, 5.14 mmol) is added over 2 hours at room temperature. After stirring for 90 minutes, the reaction mixture is treated as described in Example 1. The o-(p-tolyl)benzonitrile is thus obtained with a yield of isolated product of 95%.

EXAMPLE 5

The preparation is carried out exactly as described in Example 4, the $Pdcl_2$/dppp complex being replaced by a 1:1 mixture of palladium(II) acetate and dppp. The o-(p-tolyl)benzonitrile is thus obtained with a yield of isolated product of 94%.

EXAMPLE 6

The preparation is carried out exactly as described in Example 4 but the $PdCl_2$/dppp complex is replaced with a 1:1 mixture $PdCl_2$2LiCl and dppp. The o-(p-tolyl)benzonitrile is thus obtained with a yield of isolated product of 95%.

EXAMPLE 7

A suspension of $MnCl_2$ (0.25 g, 1.98 mmol) and LiCl (0.17 g, 3.955 mmol) in a mixture of 2 ml of anhydrous tetrahydrofuran and 0.38 ml of dimethoxyethane (3.955 mol) is stirred at room temperature until, after approximately 30 minutes, a homogeneous medium is obtained. The $PdCl_2$/dppp complex (0.0023 g, 0.1 mol %) and the o-bromobenzonitrile (0.72 g, 3 955 mmol) are then added and then a solution of p-tolylmagnesium chloride in tetrahydrofuran (1.80N, 2.86 ml, 5.14 mmol) is added over 30 minutes. After stirring for 30 minutes, the reaction mixture is treated as described in Example 4. The o-(p-tolyl)benzonitrile is thus obtained with a yield of isolated product of 95%.

What is claimed is:

1. Process for the preparation of o-(p-tolyl)benzonitrile, wherein an o-halobenzonitrile is treated with a p-tolylmagnesium halide in the presence of (i) a manganous salt and (ii) of a cocatalyst comprising a transition metal.

2. Process according to claim 1, wherein the o-halobenzonitrile is o-bromobenzonitrile.

3. Process according to claim 1, wherein the manganous salt is $MnCl_2$ or $MnCl_4Li_2$.

4. Process according to claim 1, wherein the cocatalyst comprising a transition metal is selected from the group consisting of a palladium salt, a cobalt salt, a nickel salt, and a platinum salt.

5. Process according to claim 1, wherein the cocatalyst comprising a transition metal is a palladium(II) salt.

6. Process according to claim 5, wherein the palladium(II) salt is a palladium(II) chloride or palladium(II) acetate.

7. Process according to claim 5, wherein the palladium salt is added to the reaction mixture with an organophosphorus compound comprising trivalent phosphorus.

8. Process according to claim 5, wherein the palladium(II) salt is in the form of a complex with an organophosphorus compound comprising trivalent phosphorus.

9. Process according to claim 8, wherein the palladium(II) salt is in the form of a complex between, 1,3-bis(diphenylphosphino)propane and palladium(II) chloride or acetate.

10. Process according to claim 4, wherein the nickel salt is nickel acetylacetonate.

11. Process according to claim 4, wherein the nickel salt is added to the reaction mixture with an organophosphorus compound comprising trivalent phosphorus.

12. Process according to claim 4, wherein the nickel salt is in the form of a complex with an organophosphorus compound comprising trivalent phosphorus.

13. Process according to claim 4, wherein the nickel salt is pretreated with a reducing agent.

14. Process according to claim 1, wherein the reaction is carried out in a solvent of the ether type.

15. Process according to claim 14, wherein the solvent is tetrahydrofuran.

16. Process according to claim 1, wherein the reaction is carried out in a solvent of the ether type and a cosolvent of the diether type.

17. Process according to claim 16, wherein the solvent is tetrahydrofuran and the cosolvent is dimethoxyethane.

* * * * *

UNITED STATES PATENT AND TRADEMARK OFFICE
CERTIFICATE OF CORRECTION

PATENT NO. : 6,392,080 B1
DATED : May 21, 2002
INVENTOR(S) : Alami et al.

It is certified that error appears in the above-identified patent and that said Letters Patent is hereby corrected as shown below:

<u>Title page,</u>
Item [73], Assignee, please change "Sanofi-Stnthélabo" to -- Sanofi-Synthélabo --.

Signed and Sealed this

Seventeenth Day of September, 2002

*Attest:*

JAMES E. ROGAN
*Attesting Officer*     *Director of the United States Patent and Trademark Office*